United States Patent [19]

Telschow

[11] Patent Number: 5,420,326

[45] Date of Patent: May 30, 1995

[54] BIS(PENTAERYTHRITOL PHOSPHATE ALCOHOL) HYDROGEN PHOSPHONATE

[75] Inventor: Jeffrey E. Telschow, Tarrytown, N.Y.

[73] Assignee: Akzo Nobel N.V., Arnhem, Netherlands

[21] Appl. No.: 241,890

[22] Filed: May 12, 1994

[51] Int. Cl.⁶ ............................................. C07F 9/6574
[52] U.S. Cl. ........................................ 558/74; 524/120
[58] Field of Search ................... 558/74, 119; 524/120

[56] References Cited

U.S. PATENT DOCUMENTS

| | | | |
|---|---|---|---|
| 3,789,091 | 1/1974 | Anderson et al. | 260/927 R |
| 3,873,496 | 3/1975 | Hills | 260/45.8 R |
| 3,883,478 | 5/1975 | Gresham | 260/45.8 R |
| 4,152,373 | 5/1979 | Honig et al. | 260/969 |
| 4,341,694 | 7/1982 | Halpern | 252/606 |
| 4,478,998 | 10/1984 | Halpern et al. | 544/195 |
| 4,801,625 | 1/1989 | Parr et al. | 523/179 |
| 5,235,085 | 8/1993 | Telschow et al. | 558/74 |

FOREIGN PATENT DOCUMENTS 866204  3/1971 Canada .............................. 260/346
889338  2/1962 United Kingdom .

OTHER PUBLICATIONS

Ind. Eng. Chem. Prod. Res. Dev. 1984, 23, 233–238.
J. Org. Chem., vol. 42, No. 2, 1977, 379–381.

Primary Examiner—Mary C. Lee
Assistant Examiner—Michael G. Ambroso
Attorney, Agent, or Firm—Richard P. Fennelly; Louis A. Morris

[57] ABSTRACT

Bis(pentaerythritol phosphate alcohol) hydrogen phosphonate is a flame retardant compound. Such a compound can be prepared by the transesterification of a diphenyl phosphite with pentaerythritol phosphate alcohol.

1 Claim, No Drawings

BIS(PENTAERYTHRITOL PHOSPHATE ALCOHOL) HYDROGEN PHOSPHONATE

BACKGROUND OF THE INVENTION

Various derivatives of pentaerythritol phosphate are known as flame retardant additives for polymers such as polypropylene. A recent example is provided by U.S. Pat. No. 4,801,625 to W. J. Parr et al. which describes ether, ester and carbonate derivatives of pentaerythritol phosphate. The carbonate version of such compounds can be advantageously prepared by the reaction of pentaerythritol phosphate alcohol with a dihydrocarbyl carbonate as described in U.S. Pat. No. 5,235,085.

U.S. Pat. No. 3,883,478 to J. T. Gresham discloses flame retarded polyester fibers containing a flame retardant additive of the formula:

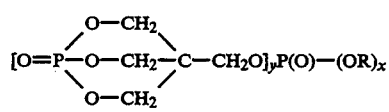

where R is an aryl radical selected from certain unsubstituted and substituted phenyl and naphthyl radicals, y is an integer of from 1 to 3, and x is 3-y.

Related U.S. Ser. No. 155,666, filed Nov. 22, 1993 describes and claims certain bis(pentaerythritol phosphate alcohol) alkylphosphonate compounds of the formula:

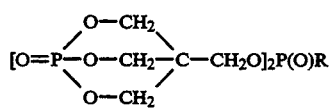

where R is alkyl, for example alkyl of from one to four carbon atoms, preferably methyl.

SUMMARY OF THE PRESENT INVENTION

The present invention relates to novel flame retardant compound which is bis(pentaerythritol phosphate alcohol) hydrogen phosphonate.

DESCRIPTION OF PREFERRED EMBODIMENTS

The present novel bis(pentaerythritol phosphate alcohol) hydrogen phosphonate is of the formula:

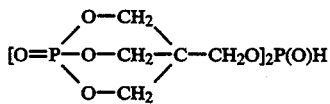

One process for forming the above-described novel compound is by the transesterification of a diphenyl phosphite with pentaerythritol phosphate alcohol which has the formula

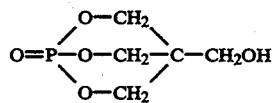

The phosphite reagent is of the formula $(ArO)_2P(O)H$, where Ar is substituted or unsubstituted phenyl. The transesterification reaction is advantageously conducted at elevated temperature (e.g., a temperature of from about 120° C. to about 250° C.), preferably in a high boiling organic solvent, such as an aryl phosphate solvent (as described in U.S. Pat. No. 5,237,085), using an appropriate transesterification catalyst (e.g., magnesium dichloride, sodium phenoxide, or the like). The reaction mixture will contain the desired crude product with a phenolic by-product. The crude product can be triturated with a solvent such as acetonitrile or methanol to give the desired, purified product.

The compound of this invention can be used as a flame retardant additive for polymers, such as the polyolefins (e.g., polypropylene).

The following Examples further illustrate the present invention.

EXAMPLE 1

Pentaerythritol phosphate alcohol (54.0 gms, 0.3 mole), diphenylphosphite (35.1 gms, 0.15 mole), sodium which had been cleaned with ethanol (69 mg, 3.0 mmoles, 2.0 mole %), and 120 mls of isopropylated diphenylphosphate (PHOSFLEX 41P brand from Akzo Chemicals Inc.) were placed in a 250 ml, 4-neck, round bottom flask, fitted with a mechanical stirrer, thermometer, 3.5 inch Vigreaux column, distillation head, and receiver with vacuum connection. A vacuum of 60 mm was applied to the reaction vessel, it was heated, and distillation of phenol began at 160° C. The pressure was decreased gradually to 2 mm and the pot temperature was increased to 180° C. over two hours. The distillate (24.7 gms) represented 87.5% of the theoretical amount of phenol expected. The reaction vessel was allowed to cool to 50° C. The product was filtered and washed three times with 40 mls of methanol and then dried in an oven at 1 mm and 100° C. The yield was 32.5 gms (53.3%) of a white powder.

EXAMPLE 2

The same type of procedure and equipment used in Examples 1 and 2 was employed in this Example. The reagents used for the reaction were 54.0 gms (0.3 mole) of pentaerythritol phosphate alcohol, 35.1 gms (0.15 mole) of diphenylphosphite, 69 mgs (3.0 mmoles, 2.0 mole %) of sodium (which had been cleaned with ethanol), and 100 mls of sulfolane which had been dried over molecular sieves.

The foregoing reagents were added to the same type of equipment described in the previous Examples. Vacuum of 50 mm was applied and the reaction mixture was heated to 150° C. during a thirty minute period. All ingredients dissolved at 100° C., and distillation began at 150° C. The distillation slowed considerably after about 15 mls had distilled from the reaction vessel. After one and one-half hours at 150° C. the pressure was gradually lowered to 4 mm. During a total of two hours at 150° C. 35.8 gms of distillate was collected or 126% of the theoretical. The excess was presumed to be sulfolane solvent. The reaction mixture was cooled and at 95° C. a heavy precipitate began to form. About 100 mls of $CH_3CN$ were added at 80° C. and the reaction mixture was stirred for a few minutes to thin the slurry, which was then cooled to 25° C. filtered and washed three time with acetone The resulting product was dried at 80° C. and 0.5 mm pressure for two hours to obtain 28.7 gms (47.0%) of a white powder.

EXAMPLE 3

The conditions used in Example 2 were repeated using 5 mole %, based on pentaerythritol phosphate alcohol, of imidazole as catalyst rather than sodium. The yield of product was 45.5%.

The foregoing Examples, which illustrate certain embodiments of the present invention, should not be construed in a limiting sense for that reason. The scope of protection sought is set forth in the claims which follow.

I claim:

1. Bis(pentaerythritol phosphate alcohol) hydrogen phosphonate.